United States Patent [19]

McCall et al.

[11] Patent Number: 4,604,315

[45] Date of Patent: Aug. 5, 1986

[54] HIGH BULK, BIAXIAL ELASTIC, HEAT SHRUNK FABRIC

[75] Inventors: Clyde A. McCall, Walhalla, S.C.; Michael J. Campbell, Roswell; William B. Dean, Cornelia, both of Ga.

[73] Assignee: Chicopee, New Brunswick, N.J.

[21] Appl. No.: 563,716

[22] Filed: Dec. 20, 1983

[51] Int. Cl.⁴ ..................... A61L 15/00; D03D 15/04; D03D 15/08; D04B 11/12
[52] U.S. Cl. .................. 428/230; 66/178 A; 66/202; 128/156; 139/421
[58] Field of Search ............. 66/178 A, 202; 139/421; 428/230; 128/156

[56] References Cited

U.S. PATENT DOCUMENTS

| | | | |
|---|---|---|---|
| 2,796,655 | 6/1957 | Stuewer | 428/230 |
| 2,810,184 | 10/1957 | Sherman | 428/230 |
| 3,040,551 | 6/1962 | Urlaub | 604/384 |
| 3,316,610 | 5/1967 | Manock | 428/230 |
| 3,669,157 | 6/1972 | Woodall et al. | 139/387 R |
| 4,173,131 | 11/1979 | Pendergrass et al. | 66/192 |

*Primary Examiner*—James C. Cannon
*Attorney, Agent, or Firm*—Nancy A. Bird

[57] ABSTRACT

A high bulk, heat shrunk fabric of texturized thermoplastic yarns in an open pattern of lock stitch knitted or leno woven yarns, said fabric exhibiting good biaxial stretch and recovery.

12 Claims, 2 Drawing Figures

HIGH BULK, BIAXIAL ELASTIC, HEAT SHRUNK FABRIC

BACKGROUND OF THE INVENTION

There are many examples of fabrics incorporating stretched elastic strands to achieve elasticity in the fabric. These fabrics suffer from a number of disadvantages, including the cost of the elastic strands and the limitations in terms of heat and chemical processing to which the final fabric with the elastic strands may be subjected. Some newer fabrics incorporate heat shrunk thermoplastic yarns which exhibit elasticity. These yarns are less expensive then elastic strands; and fabrics formed therefrom are less expensive to produce than fabrics incorporating stretched elastic strands, and are applicable to more end uses.

Many commercial elastic wrap type bandages use heat shrunk, highly stretchable thermoplastic yarns. These yarns are incorporated only in the machine direction of the fabric. In particular, the Revco elastic bandage comprises a woven fabric of heat shrunk highly stretchable nylon warp yarns and cotton weft yarns. The McMurry fabric is a knitted fabric utilizing heat shrunk highly elastic nylon warp yarns and cotton weft yarns. The Curity or Conform bandage manufactured by Kendall and described in U.S. Pat. No. 4,173,131 comprises heat shrunk texturized warp yarns in a chain loop knitted pattern of double yarns, with a complex pattern of weft yarns inlaid into the chain loops of the warp yarns. The fabric of the present invention utilizes heat shrunk, stretchable yarns in both the warp and weft direction, yielding a bandage that resists "necking down" when stretched, and which exhibits better conformability due to the elasticity of the high shrink warp and weft yarns. In one embodiment of the present invention the heat shrunk yarns are disposed in a leno weave. A leno weave has been used for example, in drapery fabrics to create an open area in the fabric. The yarns of such drapery fabrics typically are not heat shrunk or elastic. Other open weave fabrics such as screening for a tent are formed using leno weave to stabilize the open weave pattern.

BRIEF DESCRIPTION OF THE INVENTION

The present invention comprises a biaxial elastic fabric of heat shrunk texturized thermoplastic yarns. The yarns are disposed in an open pattern of locked stitch knitted or leno weave. The fabric has biaxial stretchability and recovery. In a preferred embodiment the yarns are disposed in a leno weave and in the heat shrunk fabric, the weft direction yarns are further twisted within the leno weave by the bulked double warp direction yarns turning over, and lying on their side, giving an enhanced elasticity in the weft direction. The woven fabric of the present invention has 12 to 30 warp direction yarns per inch and 4 to 12 weft direction yarns per inch in the initial knitted fabric, before shrinking, and 6–15 double warp direction yarns per inch and 4 to 12 weft direction yarns per inch in the initial leno weave fabric, before shrinking. In another preferred construction, the warp direction yarns are highly heat shrinkable direction yarns termed "power stretch" yarns and the weft direction yarns are "heat set" yarns. In the most preferred construction the yarns are polyester texturized continuous filament 150 denier yarns with 16 warp direction yarns or 8 double warp direction yarns per inch and 8 weft direction yarns per inch.

According to the method of the present invention the biaxial elastic fabric is formed by first forming an open pattern of locked stitch knitted or leno weave texturized thermoplastic yarns and thereafter applying heat to said yarns to shrink and bulk the yarns. If the open pattern formed is of a leno weave, the bulked double warp yarns will lay on their sides, further twisting the weft yarns and creating enhanced elasticity in the weft direction.

DETAILED DESCRIPTION OF THE INVENTION

The present invention comprises a heat shrunk bulky elastic fabric and the method of making the fabric. The fabric comprises texturized thermoplastic warp direction and weft direction yarns in an open pattern of lock stitch knitted or leno weave. The fabric is shrunk in both the warp and weft direction and exhibits good elasticity and recovery in all directions. The fabric has from 12 to 30 warp direction yarns per inch and 4 to 12 weft direction yarns per inch prior to heat treatment. In a leno weave the fabric may comprise 6 to 15 double warp direction yarns per inch and 4 to 12 weft direction yarns per inch, before heat treating.

The fabric has particular utility as a warp bandage, the biaxial stretchability of the fabric yielding a stretch bandage which does not "neck down" when stretched, and which exhibits excellent conformability to the particular limb, e.g., arm, or body part, e.g., head, which is wrapped. Both of these properties, in combination, yield a bandage which once wrapped does not easily move or become dislodged by movement. These combined properties are particularly useful in a bandage for use on a moveable body part such as an elbow, as repeated movement of the elbow does not cause the bandage to move in to the elbow and roll up on itself.

Figure 1:
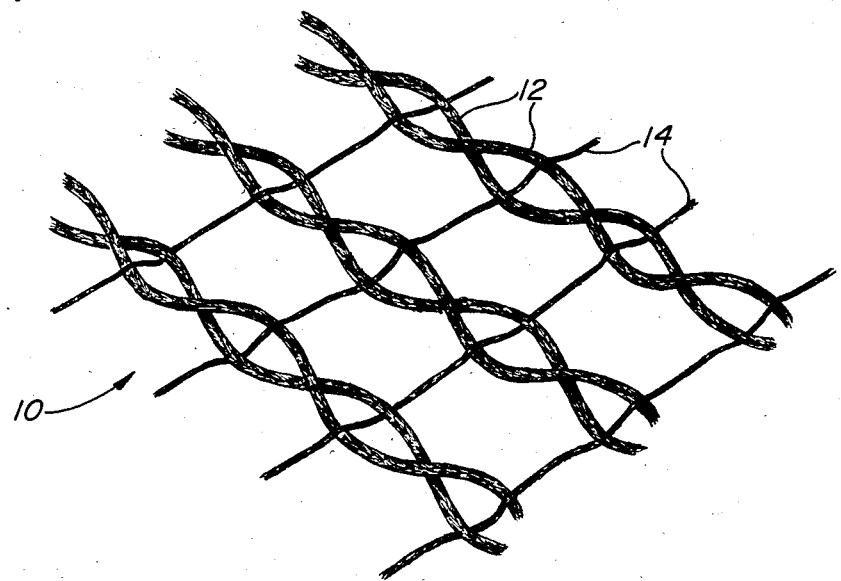
FIG. 1 is a perspective view of the schematic representation on an enlarged scale of a leno weave pattern of yarns as used in the present invention.

The fabric is formed from a locked stitch knitted or leno weave of the heat shrinkable texturized thermoplastic yarns. FIG. 1 illustrates a leno weave generally at 10. The double lock stitch pattern of warp direction yarns is shown at 12 and the weft direction yarns are shown at 14. The open pattern of the weave allows shrinkage upon heat treatment. Upon heat treatment, the bulky double warp yarns of the lock stitch leno weave pattern twist and lie on their sides, further twisting the weft yarns and yielding a fabric having enhanced elasticity in the weft direction.

Figure 2:
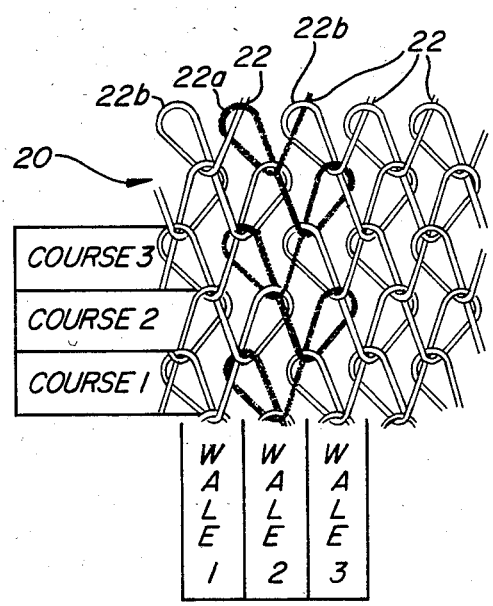
FIG. 2 is a plan view of a schematic representation on an enlarged scale of a locked stitch knitted pattern of yarns such as is used in the present invention.

FIG. 2 illustrates one example of a locked stitch knitted pattern of yarns called a single-bar warp knit, shown generally at 20, with warp direction yarns 22 lock stitched with the adjacent warp direction yarns. This lock stitch knitted pattern is a warp knit pattern wherein the courses correspond to the weft direction and wales to the warp direction as these terms are used above to describe the woven fabric of this invention. As may be seen, each warp direction yarn or wale 22a is interlocked with adjacent warp direction yarns 22b. Other suitable knit patterns include a jersey knit, a double bar raschel knit, a milano rib knit, and a ponte di roma knit and various circular knits. As used in this application, the term locked stitch indicates a yarn pattern wherein warp yarns are not easily displaced from their initial warp-wise path. This locked stitch pattern stabilizes the yarns both before and during the heat treatment and shrinkage, as well as stabilizing the yarns in the final fabric. The lock stitch leno open pattern also allows the development of enhanced elasticity in the weft direction.

The fabrics of the present invention are formed by knitting or weaving texturized thermoplastic yarns in an open locked stitch knitted or woven pattern and heat shrinking the yarns. In a preferred embodiment the yarns are polyester or nylon of 70 to 300 denier. In another preferred embodiment the warp direction yarns are highly heat shrinkable yarns sold under the name "Power Stretch" yarns which exhibit about 45 to 50% shrink in boiling water. In a still preferred embodiment comprising a leno weave, the warp direction yarns may be "Power Stretch" yarns and the weft direction yarns "heat set" yarns having about 10 to 15% shrink in boiling water. In this particular construction the fabric when shrunk exhibits almost an equal degree of stretch in both the warp and weft direction, arising from the further twisting of the weft direction yarns by the highly bulked double warp yarns.

In the fabric of the present invention, the warp direction yarns per inch may vary from 12 to 30 and the weft direction yarns per inch may vary from 4 to 12, prior to shrinking. Within this range a greater number of warp direction yarns per inch can be utilized to produce a fabric which is non-apertured in appearance, however it will also reduce the amount of stretch that can be developed in the weft direction. A lesser number of warp direction yarns per inch will allow greater shrinkage and bulking of the weft direction yarns yielding greater elasticity in the weft direction and greater stability of the weave of the heat shrunk fabric. Within the range cited, a lesser number of weft direction yarns per inch will increase the amount of stretch that can be developed in the warp direction. In a like manner, the less bulk developed in the weft direction yarns, the greater the amount of stretch that can be developed in the warp direction. Bulking of the weft direction yarns may be controlled by the use of a greater number of warp direction yarns per inch, or, in the leno weave fabrics, by the selection of lower shrink, lower bulking "heat set" yarns as opposed to higher shrink, higher bulk "power stretch" yarns for use in the weft direction.

The method of the present invention involves the steps of forming an open pattern of lock stitch knitted or leno weave heat shrinkable texturized thermoplastic yarns, and thereafter applying heat to the yarns to shrink the yarns. If the pattern used is a leno weave the bulk double warp direction yarns will lay on their side, further twisting the weft yarns and yielding a fabric with enhanced elasticity in the weft direction. The amount of heat treatment used in terms of the temperature and the time of application, may be easily determined for each type of heat shrinkable yarn used, and will vary according to the amount of elongation desired in the final fabric. In a preferred method of the present invention, utilizing polyester yarns, the knitted or woven yarns are passed through a hot air oven at 250° F. for at least 15 seconds. In a preferred method of forming the elastic conformable bandage of the fabric of the present invention the woven or knitted yarns are subject to a pre-shrink step to facilitate further processing, are scoured and rinsed and a surfactant and/or an antistat is added prior to drying and shrinking the yarns.

EXAMPLE

In the present example "power stretch" continuous filament polyester warp direction yarns were woven in a leno weave with "heat set" continuous filament polyester yarns in the weft direction. The yarns are 150 denier yarns. As initially woven the open pattern of yarns had 16 warp or 8 double woven direction yarns per inch and 6 weft direction yarns per inch. The fabric was preshrunk, scoured, rinsed, treated with surfactant, and heat shrunk at 250° F. for 15 seconds. The heat shrunk fabric exhibited at least about 180% elongation to break and about 103% "useable stretch", and about 90% recovery in the warp direction and at least about 80% elongation to break and about 83% "useable stretch", and about 70% recovery in the weft direction. The preferred construction of the 16 warp direction yarns per inch and 8 weft direction yarns per inch exhibits greater apparent stretch and recovery in the warp direction and the same apparent degree of stretch and recovery in the weft direction.

"Useable stretch" is determined by applying a 5 lb weight to the end of a 2" wide strip of fabric, measuring the stretched length after 10 seconds and calculating the percentage of elongation. The recovery is determined by thereafter removing the weight, laying the fabric sample out on a horizontal surface, and measuring the recovered length and calculating the percentage recovery.

The foregoing description and drawings are illustrative but are not to be taken as limiting. Other variations and modifications are possible without departing from the spirit and scope of the present invention.

We claim:

1. A method of making a heat shrunk, bulk, elastic fabric comprising:
   (a) forming an open pattern leno weave of highly heat shrinkable texturized theremoplastic warp direction yarns and "heat set", relatively less heat shrinkable texturized thermoplastic weft direction yarns, and
   (b) applying heat to said yarns to bulk and shrink said yarns, to yield a fabric with good elastic recovery in both warp and weft directions, the bulking of the heat-shrunk warp yarns causing said yarns to twist and lie on their sides thereby further twisting the weft yarns and creating a fabric with enhanced elasticity in the weft direction.

2. The method of claim 1 wherein said yarns are polyester.

3. The method of claim 1 wherein said open pattern of yarns formed has 12 to 30 warp direction yarns per inch and 4 to 12 weft direction yarns per inch.

4. The method of claim 1 wherein said open pattern of yarns formed has 6 to 15 double warp direction yarns per inch and 4 to 12 weft direction yarns per inch.

5. The method of claim 1 wherein said yarns are 150 denier, continuous filament yarns.

6. The method of claim 1 wherein said open pattern of yarn formed comprises 150 denier continuous filament polyester yarns with 16 warp direction yarns per inch and 8 weft direction yarns per inch.

7. The fabric produced by the method of claim 1.

8. The fabric produced by the method of claim 2.

9. The fabric produced by the method of claim 3.

10. The fabric produced by the method of claim 4.
11. The fabric produced by the method of claim 5.
12. The fabric produced by the method of claim 6, said fabric exhibiting at least about 180% elongation to break and at least about 103% usable stretch and 90% recovery in the warp direction, and about 80% elongation to break and about 80% usable stretch and about 70% recovery in the weft direction.

* * * * *